(12) United States Patent
Kong et al.

(10) Patent No.: US 9,266,067 B2
(45) Date of Patent: Feb. 23, 2016

(54) COMPOSITE SEPARATION MEMBRANE STRUCTURE FOR GAS SENSOR, GAS SENSOR APPARATUS COMPRISING THE SAME, AND METHOD AND APPARATUS FOR MEASURING GAS CONCENTRATION USING THE SAME

(75) Inventors: Hosung Kong, Seoul (KR); Hung Gu Han, Seoul (KR); Jung Wook Lee, Gyeonggi-do (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 670 days.

(21) Appl. No.: 13/566,087

(22) Filed: Aug. 3, 2012

(65) Prior Publication Data
US 2013/0138384 A1 May 30, 2013

(30) Foreign Application Priority Data
Nov. 28, 2011 (KR) ........................ 10-2011-0125350

(51) Int. Cl.
*B01D 63/08* (2006.01)
*G01N 27/06* (2006.01)
*G01N 33/28* (2006.01)
(Continued)

(52) U.S. Cl.
CPC .......... *B01D 63/087* (2013.01); *B01D 67/0048* (2013.01); *B01D 67/0079* (2013.01); *B01D 69/12* (2013.01); *B01D 69/141* (2013.01); *B01D 71/70* (2013.01); *G01N 27/06* (2013.01); *G01N 33/2841* (2013.01); *B01D 71/027* (2013.01);
(Continued)

(58) Field of Classification Search
CPC ............. B01D 63/087; B01D 67/0048; B01D 67/0079; B01D 69/12; B01D 69/141; B01D 71/70; B01D 2325/36; B01D 2325/38; B01D 71/027; G01N 27/06; G01N 33/2841; G01N 2610/00
See application file for complete search history.

(56) References Cited

U.S. PATENT DOCUMENTS 5,782,959 A * 7/1998 Yang et al. .................... 96/11
6,800,118 B2 10/2004 Kusunose et al.
(Continued)

FOREIGN PATENT DOCUMENTS

JP 05-052787 A 3/1993
JP 06-160329 A 6/1994
(Continued)

OTHER PUBLICATIONS

Young-Seok Kim et al., "Preparation of Microporous Silica Membranes for Gas Separation", Korean J. Chem. Eng., 18(1), pp. 106-112, 2001.*
(Continued)

*Primary Examiner* — Alexander Satanovsky
(74) *Attorney, Agent, or Firm* — Ladas & Parry LLP

(57) ABSTRACT

Disclosed are a composite separation membrane structure for a gas sensor for real-time monitoring of degradation of insulating oil of a power transformer, a gas sensor apparatus including the same, and a method and an apparatus for measuring gas concentration using the same. It is possible to locally diagnose whether there is a fault in the power transformer and what kind of fault occurs where in the power transformer by quantitatively measuring the concentration of several gases dissolved in the insulating oil in real time. As a result, breakdown of the power transformer may be prevented and remaining service life of the insulating oil in the power transformer may be predicted.

20 Claims, 11 Drawing Sheets

(51) Int. Cl.
  *B01D 67/00* (2006.01)
  *B01D 69/12* (2006.01)
  *B01D 69/14* (2006.01)
  *B01D 71/70* (2006.01)
  *B01D 71/02* (2006.01)

(52) U.S. Cl.
  CPC ......... *B01D 2325/36* (2013.01); *B01D 2325/38* (2013.01); *G01N 2610/00* (2013.01)

(56) References Cited

U.S. PATENT DOCUMENTS

| | | | |
|---|---|---|---|
| 7,811,362 B2 | 10/2010 | Qin | |
| 8,008,395 B2* | 8/2011 | Zoromski et al. | 524/601 |
| 2002/0054565 A1* | 5/2002 | Komaki et al. | 369/283 |
| 2003/0080049 A1* | 5/2003 | Lee et al. | 210/483 |
| 2010/0050761 A1* | 3/2010 | Lawrence et al. | 73/152.28 |

FOREIGN PATENT DOCUMENTS

| | | |
|---|---|---|
| KR | 1020010013733 A | 2/2001 |
| KR | 100342421 B1 | 6/2002 |
| KR | 1020070112014 A | 11/2007 |
| KR | 100817223 B1 | 3/2008 |
| KR | 1020110043838 A | 4/2011 |

OTHER PUBLICATIONS

Chinese Office Action dated Feb. 10, 2015; Appln. No. 201210484251.2.

Jian-You Liang; "Surface Modification of $SiO_2$ Ultrafiltration Membrane Its Application in Separation of Oil Vapor From Air", Liaoning Chemical Industry, Dec. 2010, vol. 39, No. 12, pp. 1238-1239.

Third Chinese Office Action dated Aug. 10, 2015; Appln. No. 201210484251.2.

* cited by examiner

COMPOSITE SEPARATION MEMBRANE STRUCTURE FOR GAS SENSOR, GAS SENSOR APPARATUS COMPRISING THE SAME, AND METHOD AND APPARATUS FOR MEASURING GAS CONCENTRATION USING THE SAME

CROSS-REFERENCE TO RELATED APPLICATION

This application claims priority to Korean Patent Application No. 10-2011-0125350, filed on Nov. 28, 2011, and all the benefits accruing therefrom under 35 U.S.C. §119, the contents of which in its entirety are herein incorporated by reference.

BACKGROUND

1. Field

The present disclosure relates to a composite separation membrane structure for a gas sensor, a gas sensor apparatus including the same, and a method and an apparatus for measuring gas concentration using the same. More particularly, the disclosure relates to a composite separation membrane structure for a gas sensor, a gas sensor apparatus including the same, and a method and an apparatus for measuring gas concentration using the same, which allow for real-time monitoring of degradation of insulating oil used in power equipments such as a power transformer.

2. Description of the Related Art

Power transformer is a very important power supplying equipment. In order to prevent any abrupt malfunction of power equipments and resulting blackout and economically operate the power equipments and predict their service life, a condition monitoring technology allowing for monitoring of the internal faults of the power transformer so as to prevent dangerous accidents is necessary.

The condition monitoring technologies currently used for diagnosis of internal faults that may occur in the power transformer insulating oil may include gas-in-oil analysis, measurement of power factor and water content of insulating oil, measurement of partial discharge, low-pressure surge test, and so forth.

Among the methods, the gas-in-oil analysis method may allow for detection of the degradation of insulating oil inside the power transformer as the degradation proceeds. Further, since the gas-in-oil method is technically reliable and easy for real-time application, it is employed most frequently.

The gas-in-oil analysis method will be described in more detail.

A power transformer is subject to a constant heat as an electrical coil is used in the power transformer. A local electrical breakdown inside the power transformer may result in a partial arc discharge of high temperature.

Accompanied by the situation, the hydrocarbon-based insulating oil may be thermally decomposed to generate gases such as hydrogen ($H_2$), methane ($CH_4$), acetylene ($C_2H_2$), ethylene ($C_2H_4$), etc. In particular, when there is an insulating material such as insulating paper, pressboard, Bakelite etc. around the heated portion, gases such as carbon monoxide (CO) or carbon dioxide ($CO_2$) may also be generated.

For reference, among the gases, those such as hydrogen, methane, acetylene, ethylene, ethane, propane, etc. are highly combustible, and thus are very important components in terms of diagnosis and safety management of the power transformer.

Since most of these gases are soluble in the insulating oil, it is possible to diagnose whether there is a fault in the power transformer and what kind of fault occurs where in the power transformer by extracting the gases and analyzing them quantitatively/qualitatively.

For analysis of the gases included in the insulating oil, a method of extracting an insulating oil sample from an operating power transformer, bringing the insulating oil in a laboratory, extracting gases from the insulating oil and analyzing them with a gas chromatography is generally employed.

However, this laboratory based analysis has a low reliability resulting from the human error factors that may occur during the sampling, and the analysis of results requires a lot of time as well.

Thus, attempts have been made recently to install a direct real-time measurement apparatus inside or outside of the power transformer to allow for continuous measurement and monitoring.

For example, a microfiltration filter or an ultrafiltration filter device that can filter gases in the insulating oil from the insulating oil medium may be used in order to sample gases dissolved in the insulating oil from the inside of the power transformer.

According to the study of the inventors, however, such gas sampling is made possible by applying a negative pressure using a vacuum pump at the rear side of the filter. This is because the gases dissolved in the insulating oil are extracted through the filter device across which a pressure difference is heavily applied.

However, considering the relatively short service life of the vacuum pump, this method does not seem so practical for the real-time condition monitoring technology of the power transformer whose service life should be as long as about 10-30 years.

As for another method for analysis of the gases dissolved in the insulating oil, the patent document 1 discloses an apparatus and a method for monitoring faults inside a power transformer where the faults are diagnosed by extracting and separating the gases dissolved in the insulating oil using an oil/gas separation membrane and detecting the total concentration of the gases in the insulating oil using an electrochemical gas sensor.

However, according to the study of the inventors, the patent document 1 does not specifically describe how to make the separation membrane and effects resulting from the separation membrane.

Meanwhile, a semiconductor gas sensor including a metal oxide such as tin oxide, tungsten oxide, zirconium oxide, etc. is generally known to be capable of quantitatively measuring the concentration of gas components since their electrical properties may change in response to the gas presented. The semiconductor gas sensors are frequently used for measuring pollutant gases in the air.

However, when the semiconductor gas sensor comes into direct contact with the insulating oil or comes into direct or indirect contact with oil fume produced from the insulating oil in order that the degradation of the insulating oil in the power transformer is measured, the pollutants are highly likely to contaminate the surface of the semiconductor gas sensor and to that end lead to wrong measurements.

The patent documents 2, 3 and 4 disclose an apparatus and a method for analyzing gases in insulating oil by detecting the concentration of the gases in the oil using a commercially available semiconductor gas sensor, and further disclose that a separation membrane may be selectively used for extraction and separation of the gases dissolved in the insulating oil.

However, according to the study of the inventors, the patent documents do not specifically describe how to make the separation membrane and effects resulting from the separation membrane either.

In addition, according to the study of the inventors, in the patent document 2, concentrations of a plurality of individual gases are determined sequentially, for example in a manner that the concentration of hydrogen is determined first, and then the concentration of carbon monoxide is determined. However, since this method requires special sensors capable of sensing specific gas, for example hydrogen, it is not appropriate for the generally-used semiconductor gas sensor to be used in the method.

Meanwhile, the patent document 5 presents the use of a porous PTFE polymer material having a thickness of about 1-1,000 μm and a porosity of about 5-99% for separation of gases dissolved in a fluid, and describes specific examples of stretching of the surface of the polymer material, solvent extracting or casting to obtain a porous surface.

Further, the patent document 6 presents porous polymer materials (poly(tetrafluoroethylene) and poly(tetrafluoroethylene-cohexafluoropropylene)) having a thickness of about 1-5 mm and a pore size of about 0.001-0.1 mm for extraction and separation of gases dissolved in oil medium, and describes specific examples of forming pores on the surface of an oil/gas separation membrane by bombarding the polymer material with 13.56 MHz radio frequency (RF)-type argon gas or nitrogen gas laser having an output power of about 100-500 W and a pressure of about 0.5-50 Pa for about 10-30 minutes.

However, according to the study of the inventors, even in the methods disclosed in those patent documents, it is highly likely that pressure difference across the separation membrane is inevitable. Furthermore, the processing of the separation membrane is complicated and requires a special technique.

PATENT DOCUMENTS

Patent document 1: Korean Patent No. 10-0342421
Patent document 2: Korean Patent Publication No. 10-2007-0112014
Patent document 3: Japanese Patent Publication No. H5-52787
Patent document 4: Japanese Patent Publication No. H6-160329
Patent document 5: U.S. Pat. No. 6,800,118
Patent document 6: U.S. Pat. No. 7,811,362

SUMMARY

The present disclosure is directed to a composite separation membrane structure for a gas sensor, which includes a separation membrane for separating an insulating oil and gases dissolved therein, used along with a semiconductor gas sensor, and a gas sensor apparatus including the composite separation membrane. The insulating oil may not pass but the gases in the insulating oil may pass through the composite separation membrane, contamination due to the insulating oil medium and water included therein may be prevented, pressure difference may be small across the composite separation membrane structure, and its mechanical strength may not be lowered.

The present disclosure is also directed to a method and an apparatus for measuring gas concentration, which allow for easy measurement of a concentration of an individual kind of gas among the gases in the insulating oil with high reliability using a generally-used semiconductor gas sensor, without being subject to difficulties of using or choosing specific semiconductor gas sensors reacting with specific gases.

In embodiments, provided is a composite separation membrane structure for a gas sensor including: a support having a mesh structure; a coating layer of a porous sol-gel material disposed on the support; and a self-assembled monolayer disposed on the coating layer of the porous sol-gel material.

In an exemplary embodiment, the self-assembled monolayer may be both oleophobic and hydrophobic.

In an exemplary embodiment, the self-assembled monolayer may be made of a fluorohydrocarbon-based silane.

In an exemplary embodiment, the support may be a metal or ceramic support.

In an exemplary embodiment, the porous sol-gel material may be an organometal compound or ceramic.

In an exemplary embodiment, the porous sol-gel material may be a polymer material obtained by the sol-gel method from a precursor of at least one alkoxysilane selected from a group consisting of methyltrimethoxysilane, tetramethoxysilane, dimethyldimethoxysilane, tetraethoxysilane, methyltriethoxysilane, dimethyldiethoxysilane, phenyltrimethoxysilane, diphenyldimethoxysilane, phenyltriethoxysilane, diphenyldiethoxysilane, decyltrimethoxysilane and isobutyltrimethoxysilane; or alkoxy compound represented by the formula $M(OR)_x$ [wherein M is a metal or metalloid such as titanium, zirconium, nickel, aluminum, lead, boron, etc. and R is $C_{1-10}$ alkyl]; or a combination thereof.

In embodiments, provided is a gas sensor apparatus including: a semiconductor gas sensor; and said composite separation membrane structure disposed apart from the semiconductor gas sensor.

In an exemplary embodiment, the gas sensor apparatus may include: a housing wherein the semiconductor gas sensor and the composite separation membrane structure are accommodated or mounted; a lower plate supporting the semiconductor gas sensor; and an upper plate covering the composite separation membrane structure, and the lower plate and the upper plate are respectively engaged with the housing.

In an exemplary embodiment, the gas sensor apparatus may include: one said composite separation membrane structure; and a semiconductor gas sensor array wherein two or more of the semiconductor gas sensors are arranged.

In an exemplary embodiment, the gas sensor apparatus may include: a first housing wherein the semiconductor gas sensor array is accommodated or mounted; a second housing wherein the composite separation membrane structure is accommodated or mounted; an end cap engaged with a lower portion of the first housing; and an adapter engaged with an upper portion of the second housing, and the first housing and the second housing are engaged with each other.

In an exemplary embodiment, the gas sensor apparatus may further include a gas seal pad disposed on one or both sides of the composite separation membrane structure.

In an exemplary embodiment, the gas sensor apparatus may further include a seal member in the housing.

In an exemplary embodiment, the gas sensor apparatus may further comprise a connecting member connecting the first housing with the end cap.

In an exemplary embodiment, the gas sensor apparatus may perform sensing in contact with the insulating oil in the power transformer or a fume of the insulating oil in the power transformer.

In embodiments, provided is a method for measuring gas concentration, including: obtaining a sensor resistance value $R_s$ by sensing gases dissolved in insulating oil using at least one semiconductor gas sensor; and obtaining a concentration of an individual gas dissolved in the insulating oil from the sensor resistance value $R_s$ using the Equation 1:

$$[\text{Log } G]_i = [k_{ij}]^{-1}[[\text{Log}(R_s/R_0)]_i - [\Sigma a_{ij}]_i](i,j=1,\ldots,n) \quad \text{[Equation 1]}$$

wherein $R_0$ is a sensor resistance value measured when a concentration of an individual gas is fixed under clean air condition without other gases to be measured except the individual gas, which is a constant;

$R_s/R_0$ is a sensor resistance ratio, i is a number assigned to the individual semiconductor gas sensors used for the measurement of gas concentration, j is a number assigned to the individual gases subjected to the gas concentration measurement, n is a total number of gases measured, G is a concentration of an individual gas to be measured, $[\text{Log } G]_i$ is a matrix of the logarithm of concentrations of individual gases to be measured, $k_{ij}$ is a change rate of the logarithm of the sensor resistance ratio depending on the change of the logarithm of concentration of the j-th gas at the i-th semiconductor gas sensor, which is a constant determined by the i-th semiconductor gas sensor depending on the j-th gas or a value calibrated from the constant, $[k_{ij}]^{-1}$ is an inverse matrix of a matrix of $k_{ij}$, with i and j varying from 1 to n respectively, $[\text{Log}(R_s/R_0)]_i$ is a matrix of the logarithm of the sensor resistance ratio with i varying from 1 to n, $a_{ij}$ is a logarithm of sensor resistance ratio at which minimum concentration of the j-th gas may be measured by the i-th semiconductor gas sensor, which is a constant determined by the i-th semiconductor gas sensor depending on the j-th gas or a value calibrated from the constant, $\Sigma a_{ij}$ is a sum of $a_{ij}$ with i being fixed and j varying from 1 to n, and $[\Sigma a_{ij}]_i$ is a matrix of $\Sigma a_{ij}$ with i varying from 1 to n.

In an exemplary embodiment, in the method for measuring gas concentration a gas sensor apparatus is used, the gas sensor apparatus including: the semiconductor gas sensor; and said composite separation membrane structure disposed apart from the semiconductor gas sensor.

In embodiments, provided is an apparatus for measuring gas concentration including: at least one semiconductor gas sensor; and a calculation device obtaining a concentration of an individual gas dissolved in insulating oil using the Equation 1 from a resistance value $R_s$, which is obtained by sensing the gases dissolved in the insulating oil using the semiconductor gas sensor.

In an exemplary embodiment, the apparatus for measuring gas concentration may further include the gas sensor apparatus including the semiconductor gas sensor; and said composite separation membrane structure disposed apart from the semiconductor gas sensor, and the sensor resistance value $R_s$ being obtained using the semiconductor gas sensor of the gas sensor apparatus.

BRIEF DESCRIPTION OF THE DRAWINGS

The above and other aspects, features and advantages of the disclosed exemplary embodiments will be more apparent from the following detailed description taken in conjunction with the accompanying drawings in which.

[Description of Main Elements]

Figure 1:
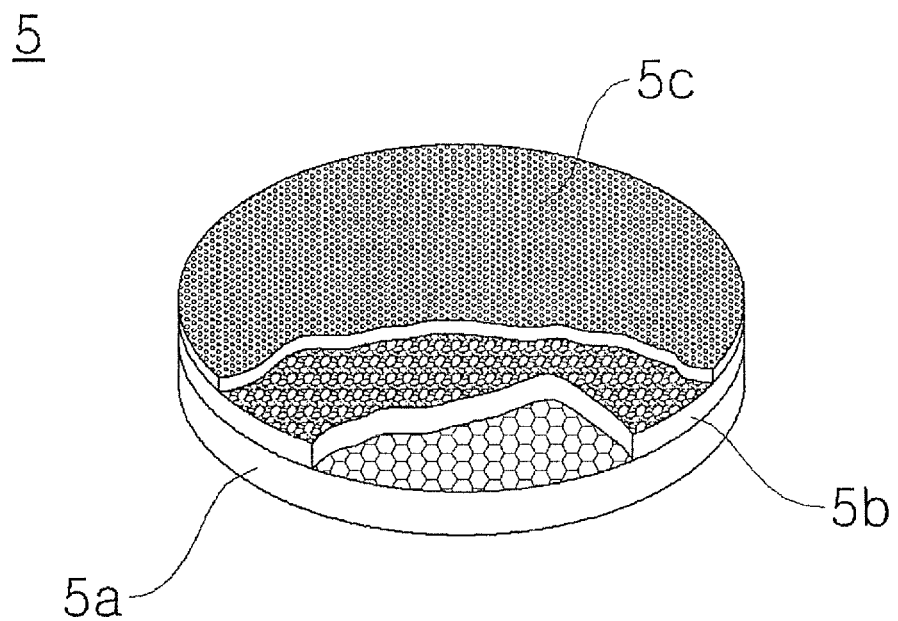
FIG. 1 schematically shows a composite separation membrane structure according to an exemplary embodiment.

| | |
|---|---|
| 1: semiconductor gas sensor | 2: housing |
| 3: upper plate | 4: lower plate |
| 5: composite separation membrane structure | |
| 5a: support having a mesh structure | |
| 5b: layer of porous sol-gel material | |
| 5c: self-assembled monolayer | |
| 6: gas seal pad | 7: O-ring (seal member) |
| 8, 9: flat-headed bolt | |
| 10, 10': gate valve for discharging dissolved gases | |
| 11, 11': pipe socket | 12, 12': O-ring (seal member) |
| 13, 13': gas sensor apparatus | |
| 14: transformer body | 15: first housing |
| 16: couple ring | 17: end cap |
| 18: O-ring (seal member) | 19: semiconductor gas sensor array |
| 20: second housing | 21: gas seal pad |
| 22: composite separation membrane structure | |
| 22a: support having a mesh structure | |
| 22b: layer of porous sol-gel material | |
| 22c: self-assembled monolayer | 23: adapter |
| 24, 25: flat-headed bolt | 26: test box |
| 27: gas sensor apparatus with composite separation membrane structure | |
| 28: gas sensor apparatus with no composite separation membrane structure | |
| 29: electrochemical gas sensor | |
| 30: carbon dioxide pressure vessel | |
| 31: pressure controller | |
| 32: on/off valve for gas injection | |
| 33: on/off valve for gas discharge | |

DETAILED DESCRIPTION

Exemplary embodiments now will be described more fully hereinafter with reference to the accompanying drawings, in which exemplary embodiments are shown. The present disclosure may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art. In the description, details of well-known features and techniques may be omitted to avoid unnecessarily obscuring the presented embodiments.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise.

Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals denote like elements. The shape, size and regions, and the like, of the drawing may be exaggerated for clarity.

Hereinafter, a composite separation membrane structure for a gas sensor, a gas sensor apparatus using the same, and a method and an apparatus for measuring gas concentration using the same according to exemplary embodiments will be described in detail.

Using an inexpensive, commercially available (i.e. generally-used) semiconductor gas sensor for quantitative real-time monitoring of degradation of insulating oil used in power equipments such as a power transformer will have a great economic value and innovatively replace the existing condition monitoring technology.

However, in order to use a commercially available semiconductor gas sensor for real-time quantitative monitoring of gases dissolved in the insulating oil, a separation membrane for extraction and separation of the dissolved gases is necessary. The separation membrane should be a membrane through which hydrocarbon-based insulating oil may not pass but low-molecular-weight gases dissolved in the oil to be measured may physically pass.

Further, a pressure difference across the separation membrane, which is in contact with the insulating oil medium in the power transformer or with a fume present in a empty space in an upper portion of the power transformer, needs to be minimized so that it is not necessary to artificially induce flow through the separation membrane by applying a negative pressure, etc.

Furthermore, it is necessary to improve a durability of the separation membrane by enhancing a mechanical strength of the separation membrane although the pressure difference across the separation membrane is small.

In addition, a contamination of the separation membrane surface due to physical or chemical adsorption of the insulating oil medium and water included in the insulating oil should be prevented in terms of durability and reliability.

In the embodiments, provided is a three-layered composite separation membrane structure including a separation membrane for separating insulating oil and gases dissolved therein, which is used together with a semiconductor gas sensor, wherein a porous sol-gel material is coated on a mesh-structured support (for example, a lattice-type of fine size), and then a material having such fine pores through which only the gases in the insulating oil may pass is coated with a very small thickness on the surface of the porous sol-gel material.

FIG. 1 schematically shows a composite separation membrane structure according to an exemplary embodiment.

As shown in FIG. 1, a composite separation membrane structure 5 according to an exemplary embodiment comprises a support 5a having a mesh structure, a coating layer 5b of a porous sol-gel material disposed on the support, the porous sol-gel material being a porous material obtained by a sol-gel method (i.e., a porous sol-gel material); and a self-assembled monolayer 5c disposed on the coating layer of the porous sol-gel material.

First, the self-assembled monolayer 5c will be described. The self-assembled monolayer 5c is an organized layer of molecules having a head group and a tail with a functional group attached at the end of the tail. The self-assembled monolayer has a small thickness, for example, of about 1-10 μm, and has a porous surface with very fine pores with a pore size of nanometer order (for example about 10-50 nm). Therefore, insulating oil medium having a relatively, large molecular weight may not pass through the self-assembled monolayer, but gases dissolved in the insulating oil may pass through the self-assembled monolayer.

In an exemplary embodiment, the self-assembled monolayer may be both oleophobic and hydrophobic. When the self-assembled monolayer is both oleophobic and hydrophobic, a contamination of the separation membrane surface due to physical or chemical adsorption of degraded insulating oil and water included in the insulating oil may be prevented.

The self-assembled monolayer which is both oleophobic and hydrophobic is known in the related art. Non-limiting examples of both oleophobic and hydrophobic self-assembled monolayer may include a fluorohydrocarbon-based silane.

The fluorohydrocarbon-based silane may be, for example, 3M's Novec Coating EGC-1720, which is a transparent, low-viscosity solution of a fluorosilane polymer dissolved in a hydrofluoroether solvent.

Meanwhile, if the self-assembled monolayer is directly coated on a semiconductor gas sensor surface, several undesired problems may occur. That is, commercially available semiconductor gas sensors generally have a heating wire embedded in the sensors and may be heated to a certain temperature in order to improve detection sensitivity. Thus, it is necessary for the self-assembled monolayer to keep a distance from the heating wire to endure such temperature. Further, it is also necessary to reinforce the self-assembled monolayer which is very thin and has weak mechanical strength.

The mechanical strength of the self-assembled monolayer is reinforced as follows.

First, the support 5a having a mesh structure is formed at the lowest portion of the self-assembled monolayer 5c.

In an exemplary embodiment, the support having a mesh structure may be a metal mesh or a ceramic mesh. A metal mesh may be used because its manufacturing is easy and costs low.

As for a non-limiting example, a mesh interval may be about 1-100 μm in length and breadth, and the support may have a thickness of about 0.05-1 mm.

When strength is reinforced with the support 5a having a mesh structure, it may not be easy to form the self-assembled monolayer 5c directly on the support 5a and there may also be a need of further strength reinforcement.

Therefore, the coating layer 5b of a porous sol-gel material, i.e. a porous material obtained by the sol-gel method is formed on the surface of the support 5a having a mesh structure between the support 5a and the self-assembled monolayer 5c. The self-assembled monolayer 5c is coated on the coating layer 5b, as described above.

The coating layer 5b of the porous sol-gel material not only makes it easy to form the self-assembled monolayer 5c but also has larger pores than the fine pores of the self-assembled monolayer 5c since the porous sol-gel material is obtained by the sol-gel method, i.e. gelation of sol.

For reference, the sol-gel method is a well known process in the art where a colloidal state (sol) is prepared using a precursor and the sol is changed to a liquid state (gel) through gelation to obtain a network structure, i.e., a porous sol-gel material.

In an exemplary embodiment, the porous sol-gel material is a polymer material obtained by the sol-gel method from a precursor of at least one alkoxysilane selected from a group consisting of methyltrimethoxysilane, tetramethoxysilane, dimethyldimethoxysilane, tetraethoxysilane, methyltriethoxysilane, dimethyldiethoxysilane, phenyltrimethoxysilane, diphenyldimethoxysilane, phenyltriethoxysilane, diphenyldiethoxysilane, decyltrimethoxysilane and isobutyltrimethoxysilane; or alkoxy compound represented by the formula $M(OR)_x$ [wherein M is a metal or metalloid such as titanium, zirconium, nickel, aluminum, lead, boron, etc. and R is $C_{1-10}$ alkyl]; or a combination thereof. When those polymer materials are used, durability, heat resistance and/or adhesivity, etc. may be improved.

As for a non-limiting example, the coating layer of the porous sol-gel material may have a thickness of about 10-1,000 nm.

Next, a gas sensor apparatus comprising the composite separation membrane structure will be described.

Figure 2A:
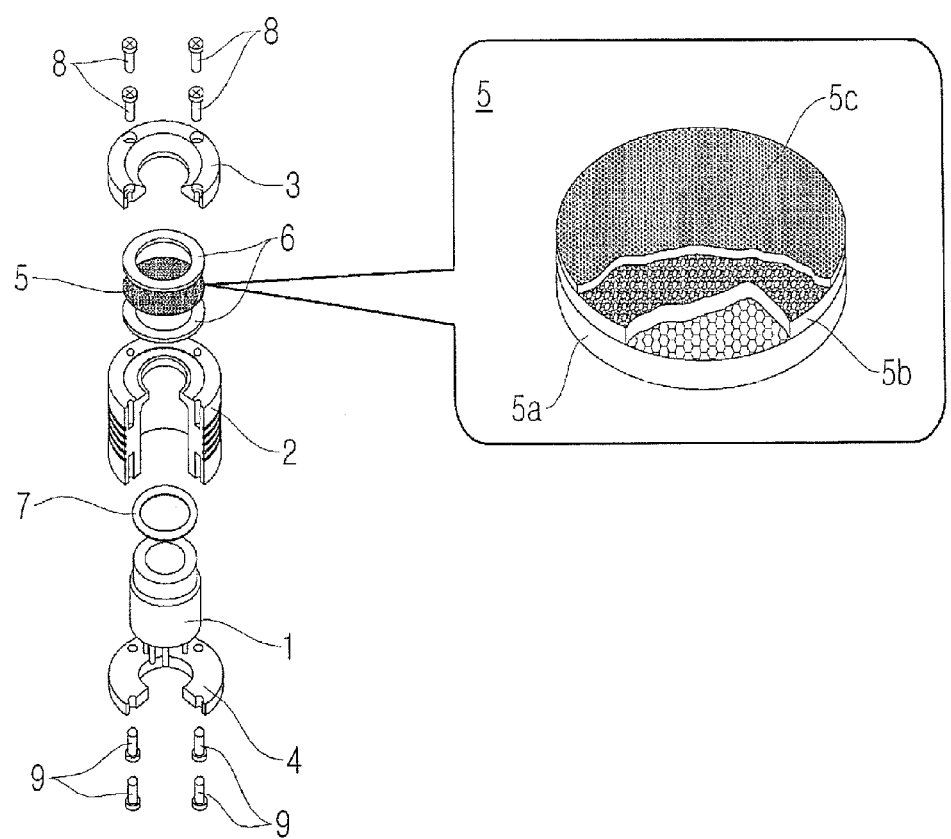
FIGS. 2a-2c schematically show a configuration of a gas sensor apparatus according to an exemplary embodiment.
Figure 2B:
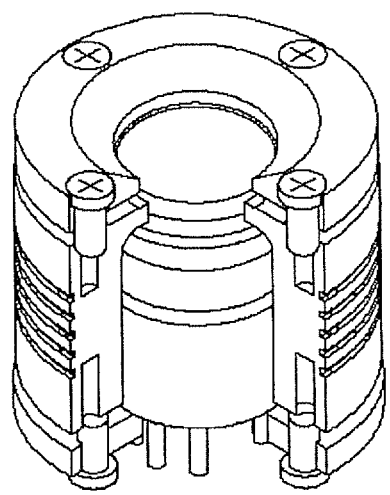
Figure 2C:
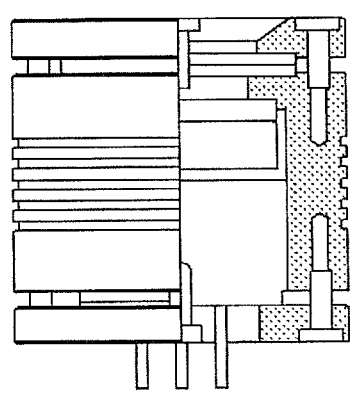

FIGS. 2a-2c schematically show the configuration of a gas sensor apparatus according to an exemplary embodiment. FIG. 2a is an exploded view of the gas sensor apparatus, FIG. 2b shows a state where the components shown in FIG. 2a are assembled, and FIG. 2c is a cross-sectional side view of FIG. 2b.

As seen in FIG. 2a, a gas sensor apparatus according to an exemplary embodiment comprises a semiconductor gas sensor 1 and the above-described composite separation membrane structure 5 disposed apart from the semiconductor gas sensor 1 with a certain distance.

As described above, commercially available semiconductor gas sensors may have a heating wire embedded in the sensors and are heated to a certain temperature to improve detection sensitivity. Thus, disposing the composite separation membrane structure 5 apart from the semiconductor gas sensor 1 with a distance allows the composite separation membrane structure 5 to keep a distance from the heating wire in the sensors.

Specifically, in the gas sensor apparatus, the semiconductor gas sensor 1 is accommodated in a housing 2 (for example, cylindrical in shape) serving as a body. Further, the composite separation membrane structure 5 is mounted on the upper portion of the housing 2 spaced apart with a distance from the semiconductor gas sensor 1. The semiconductor gas sensor 1 is supported by a lower plate 4, and the composite separation membrane structure 5 is covered by an upper plate 3. The upper plate 3 and the lower plate 4 are respectively engaged with the housing 2 by using engaging means, for example, flat-headed bolts 8, 9 (see FIGS. 2b and 2c).

A seal member such as an O-ring 7 may be provided on the semiconductor gas sensor 1 in the housing 2.

In addition, a gas seal pad 6, for example a silicone pad, may be disposed on one or both sides of the composite separation membrane structure 5.

Figure 3A:
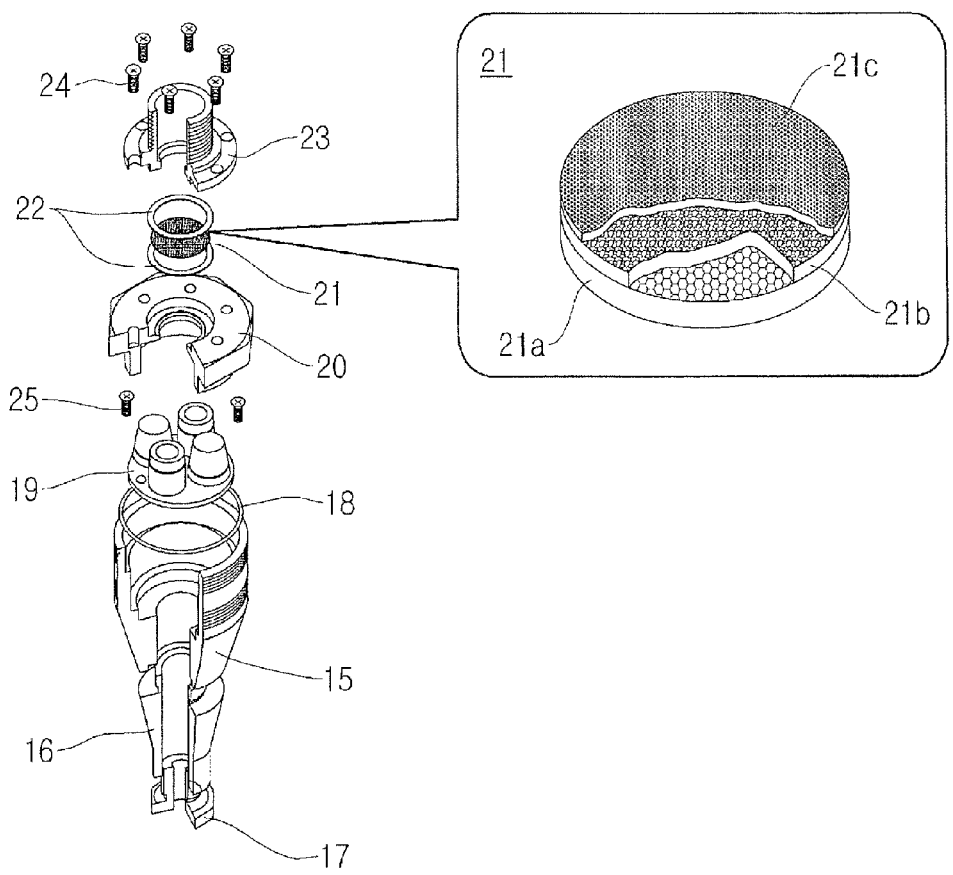
FIGS. 3a-3c schematically show a configuration of a gas sensor apparatus according to another exemplary embodiment.
Figure 3B:
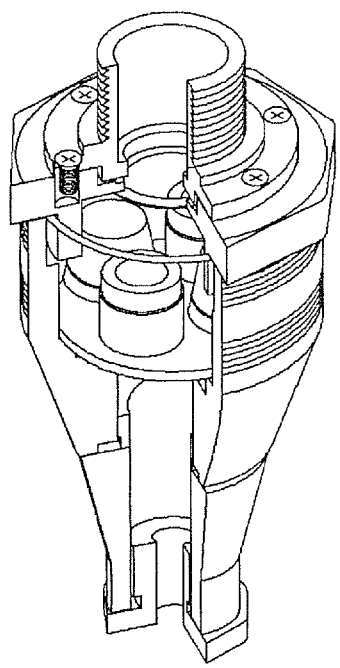
Figure 3C:
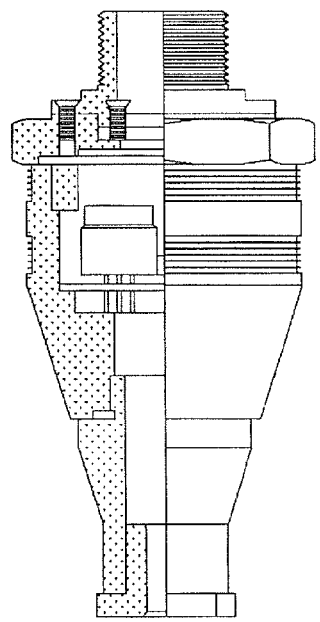

Meanwhile, when it is desired to measure several different gases dissolved in the insulating oil at the same time using a plurality of semiconductor gas sensors, the gas sensor apparatus shown in FIGS. 2a-2c may be modified as in FIGS. 3a-3c so as to effectively measure the several different gases dissolved in the insulating oil.

FIGS. 3a-3c schematically show the configuration of a gas sensor apparatus according to another exemplary embodiment. FIG. 3a is an exploded view of the gas sensor apparatus, FIG. 3b shows a state where the components shown in FIG. 3a are assembled, and FIG. 3c is a cross-sectional side view of FIG. 3b.

Referring to FIGS. 3a-3c, a plurality of semiconductor gas sensors are arranged as an array 19 and one said composite separation membrane structure 21 is disposed on the sensor array 19 to configure an integrated gas sensor apparatus. As described above, the composite separation membrane structure 21 comprises a support 21a having a mesh structure, a coating layer 21b of a porous sol-gel material disposed on the support 21a, and a self-assembled monolayer 21c disposed on the coating layer 21b of the porous sol-gel material.

The gas sensor apparatus may comprise a first housing 15 serving as a body wherein the array 19 of the plurality of semiconductor gas sensors is accommodated, a second housing 20 wherein the composite separation membrane structure is mounted, an end cap 17 engaged with a lower portion of the first housing 15 for example by bolts, and an adapter 23 engaged with an upper portion of the second housing 20. The adapter 23 is an adapter for connection with a power transformer.

A couple ring 16 which is a connecting member may be further disposed between the end cap 17 and the first housing 15. The couple ring 16 may be engaged with the first housing 15 and the end cap 17 respectively by bolts.

The first housing 15 and the second housing 20 may be engaged with each other by bolts. Also, the second housing 20 and the adapter 23 may be engaged by engaging means, e.g. flat-headed bolts 24. And, the array 19 may also be fixed in the first housing via engaging means, e.g. flat-headed bolts 25.

Next, an example of measuring gas concentration by connecting the gas sensor apparatus to a power transformer will be described.

Figure 4:
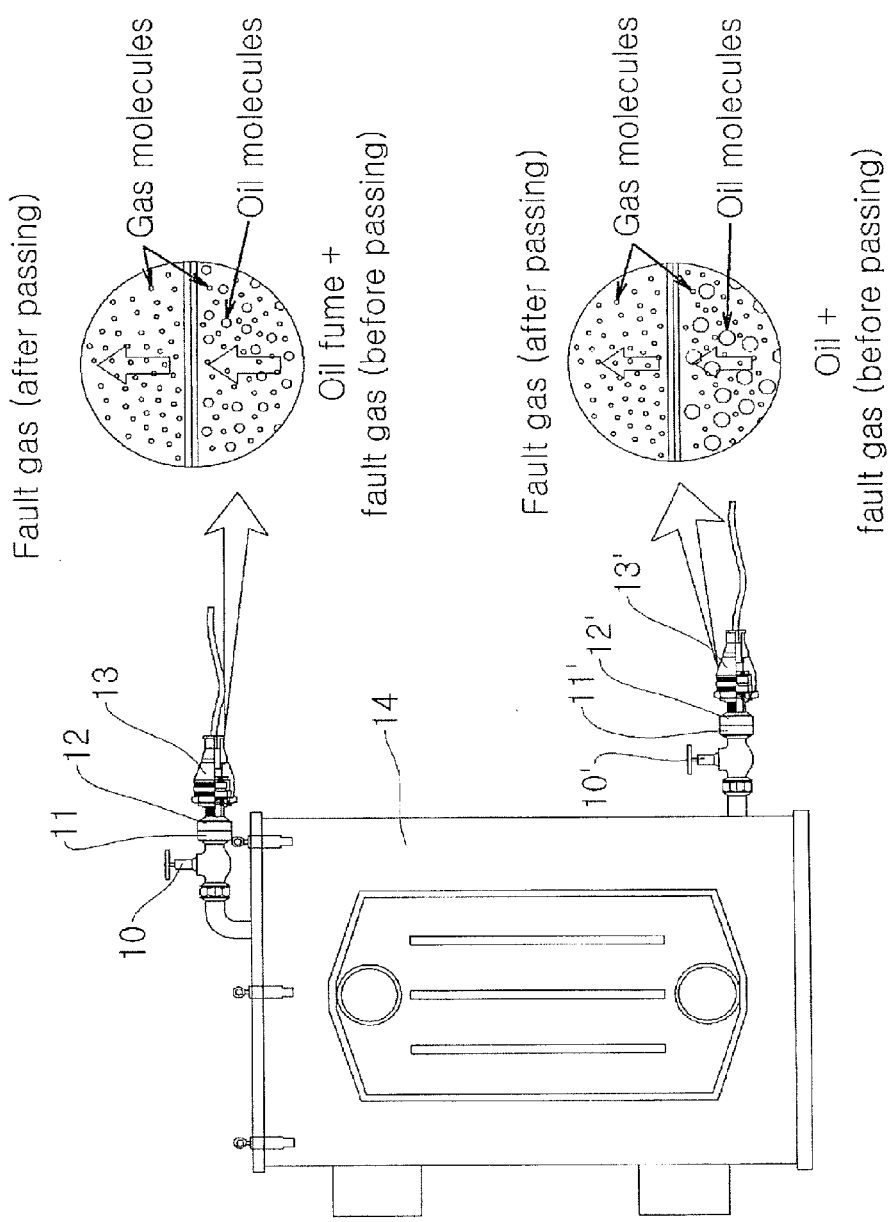
FIG. 4 schematically shows an example wherein a gas sensor apparatus according to an exemplary embodiment is connected to a power transformer.

FIG. 4 schematically shows an example wherein the gas sensor apparatus according to an exemplary embodiment is connected to a power transformer;

As seen in FIG. 4, the gas sensor apparatus may perform sensing in contact with the insulating oil of the power transformer or a fume of the insulating oil in the power transformer.

Specifically, the gas sensor apparatus 13, 13' according to an exemplary embodiment may be connected at an upper portion or a lower portion of the power transformer body 14.

When the insulating oil is not filled up to the upper portion of the power transformer body 14, an empty space is made at the upper portion of the power transformer body 14. When oil fume are present in the space under a gas equilibrium condition between the insulating oil and the gal in the insulating oil, it is more advantageous to use the gas sensor apparatus 13 according to an exemplary embodiment. A gate valve 10 for discharging the dissolved gases may be disposed at the upper portion of the power transformer body 14, and the gas sensor apparatus 13 may be connected after a pipe socket 11 and an O-ring (seal member) 12 so as to sense the gases dissolved in the insulating oil.

When there is no such empty space in the power transformer body 14, a gate valve 10' for discharging the dissolved gases may be disposed at a random portion of the power transformer body 14 (for example, at the lower portion), and the gas sensor apparatus 13 may be connected after a pipe socket 11' and an O-ring (seal member) 12' so that the gases dissolved in the insulating oil may be sensed directly in a condition that the gas sensor apparatus 13 is in contact with the insulating oil medium.

Next, a method and an apparatus for measuring gas concentration according to exemplary embodiments will be described in detail.

In order to quantitatively measure the gases dissolved in insulating oil in real time using commercially available semiconductor gas sensors, it is needed to avoid any inconveniences or difficulties of having to use or choose specific semiconductor gas sensors giving sensor output values reacting with specific gases. Actually, the commercially available semiconductor gas sensors do not give their sensor output values in response only to a specific gas, for example, hydrogen, but give sensor output values reacting with all the gases dissolved in the insulating oil.

With respect to economical usefulness, the generally-used semiconductor gas sensor giving sensor output values in response to different gases should be used in a gas sensor apparatus. Further, it is needed that the concentration of the individual gases should be measured easily with high reliability when the generally-used semiconductor gas sensors are used.

Thus, in an exemplary embodiment, concentrations of the individual kind of gases dissolved in the insulating oil may be independently calculated based on the measurements from a plurality of generally-used semiconductor gas sensors measuring the mixed gases in the insulating oil.

For this, a plurality of generally-used gas sensors are used, and the numbers of the generally-used gas sensors are the same as the kinds of gases dissolved in the insulating oil.

As explained below regarding Equation 1, concentrations of the individual kinds of gases dissolved in the insulating oil may be determined through calculation using [Equation 1] based on the sensor resistance ratio of the plurality of sensors used for measurement and constants determined according to the gas sensor and gas.

That is to say, in an exemplary embodiment, a sensor resistance value $R_s$ is obtained by sensing the gases dissolved in the insulating oil using at least one generally-used semiconductor gas sensors. From the resistance value $R_s$, the concentrations of the individual gases dissolved in the insulating oil are obtained by using the Equation 1:

$$[\text{Log } G]_i = [k_{ij}]^{-1} [[\text{Log}(R_s/R_0)]_i - [\Sigma a_{ij}]_i] (i,j=1,\ldots,n) \quad \text{[Equation 1]}$$

wherein $R_0$ is a sensor resistance value measured when a concentration of an individual gas is fixed, for example as 1,000 ppm, under clean air condition without other gases to be measured except the individual gas, which is a constant;

$R_s/R_0$ is a sensor resistance ratio, i is a number assigned to the individual semiconductor gas sensors used for the measurement of gas concentration, j is a number assigned to the individual gases subjected to the gas concentration measurement, n is a total number of gases measured, G is a concentration of an individual gas to be measured,

[Log G]$_i$ is a matrix of the logarithm of concentrations of individual gases to be measured, $k_{ij}$ is a change rate of the logarithm of the sensor resistance ratio depending on the change of the logarithm of concentration of the j-th gas at the i-th semiconductor gas sensor, which is a constant determined by the i-th semiconductor gas sensor depending on the j-th gas or a value calibrated from the constant, $[k_{ij}]^{-1}$ is an inverse matrix of a matrix of $k_{ij}$, with i and j varying from 1 to n respectively,

[Log($R_s/R_0$)] is a matrix of the logarithm of the sensor resistance ratio with i varying from 1 to n, $a_{ij}$ is a logarithm of sensor resistance ratio at which minimum concentration of the j-th gas may be measured by the i-th semiconductor gas sensor, which is a constant determined by the i-th semiconductor gas sensor depending on the j-th gas or a value calibrated from the constant, $\Sigma a_{ij}$ is a sum of $a_{ij}$ with i being fixed and j varying from 1 to n, and $[\Sigma a_{ij}]_i$ is a matrix of $\Sigma a_{ij}$ with i varying from 1 to n.

Figure 5:
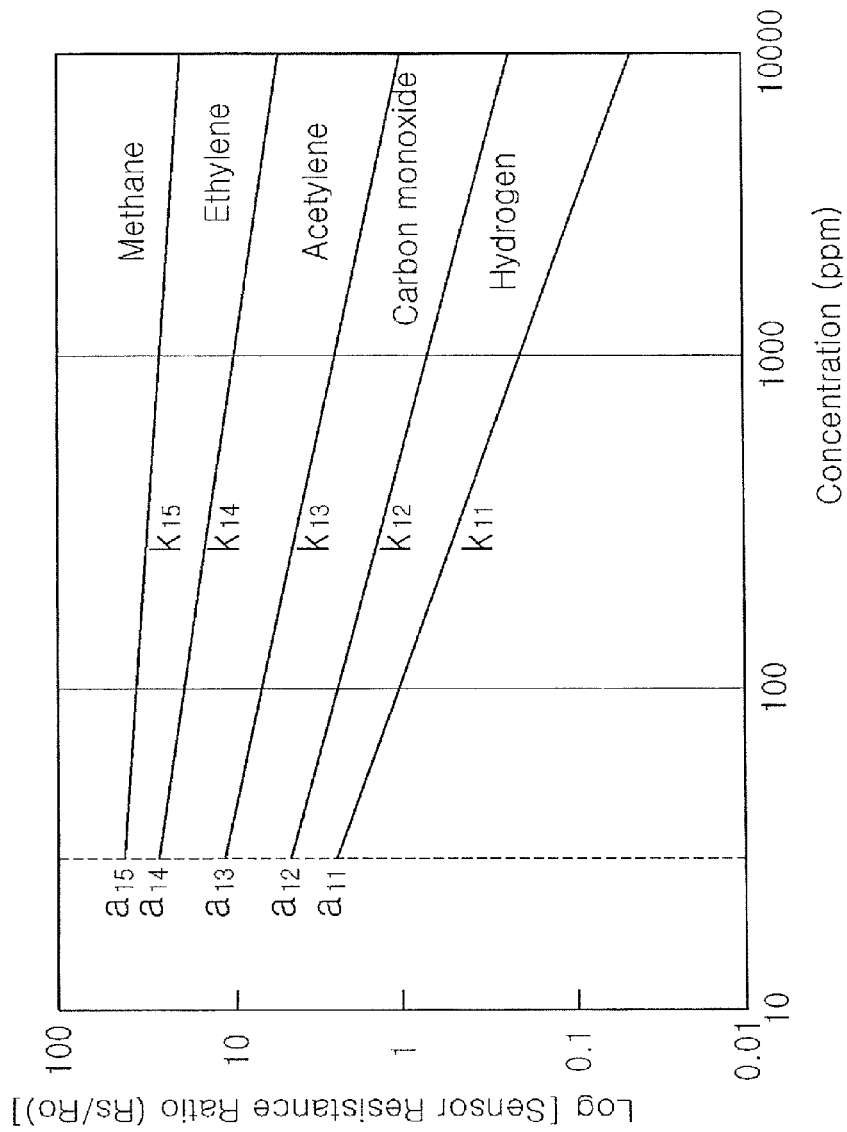
FIG. 5 is a graph showing an example of the sensor resistance ratio ready-measured for different gases and different concentrations using a commercially available semiconductor gas sensor which is to be used in an exemplary embodiment.

In the present disclosure, the $k_{ij}$ value or the $a_{ij}$ value is a constant according to the generally-used semiconductor sensor provided by the semiconductor sensor manufacturer or provider (see FIG. 5). When the generally-used semiconductor sensor is used in the embodiments, if necessary, the value may also be obtained by further calibrating the constant as will be described later. Accordingly, the $k_{ij}$ value or the $a_{ij}$ value is a constant determined at the i-th semiconductor gas sensor depending on the j-th gas or a value calibrated from the constant.

Further, the $R_0$ value is a known sensor resistance value, i.e. a constant sensor resistance value measured when a concentration of an individual gas is fixed, for example, at 1000 ppm under clean air condition without other gases to be measured except the individual gas.

In the method for measuring gas concentration according to an exemplary embodiment, a semiconductor gas sensor in said gas sensor apparatus as described above may be used for the generally-used gas sensor.

In an exemplary embodiment, the concentrations of the individual gases dissolved in the insulating oil may be measured quantitatively using an apparatus for measuring gas concentration. The apparatus for measuring gas concentration may include at least one generally-used semiconductor gas sensors and a calculation device which obtains the concentrations of the individual gases dissolved in the insulating oil from the resistance value $R_s$ using the [Equation 1]. Herein $R_s$ is obtained by sensing the gases dissolved in the insulating oil using the generally-used semiconductor gas sensors.

In an exemplary embodiment, the apparatus for measuring gas concentration may also include the gas sensor apparatus as described above, and the sensor resistance value $R_s$ may be obtained using the semiconductor gas sensor of the gas sensor apparatus.

For convenience of understanding of the Equation 1, an example will be described wherein the number of the sensors is 5 (i.e., i=1, 2, 3, 4, 5) and the number of the gases is 5 (i.e., j=1, 2, 3, 4, 5). That is, in exemplary embodiments, the number of the semiconductor gas sensors i is set identical to the number of the gases to be measured j.

It is assumed that 5 different gases, for example, hydrogen ($H_2$), carbon monoxide (CO), acetylene ($C_2H_2$), ethylene ($C_2H_4$) and methane ($CH_4$) gases are dissolved in power transformer insulating oil. Further, for convenience of understanding, it is assumed that a commercially available semiconductor gas sensor is used, the sensor output resistance $R_s$ measured for the different gases using the commercially available semiconductor gas sensor being shown as in FIG. 5.

FIG. 5 is a graph showing an example of the sensor resistance ratio ready-measured for different gases and different concentrations using a commercially available semiconductor gas sensor which is to be used in an exemplary embodiment. This kind of example graph is provided by the providers or manufacturers of the commercially available semiconductor gas sensor for calibration of the actually measured data.

In FIG. 5, the x-axis shows concentration (ppm) and the y-axis shows logarithm of sensor resistance ratio [Log($R_s/R_0$)]. $R_0$ is a constant sensor resistance value measured when a concentrations of an individual gas is fixed, for example, at 1000 ppm under clean air condition without other gases to be measured except the individual gas $R_s$ is a resistance value measured by the commercially available semiconductor gas sensor under an arbitrary gas conditions (i.e., given gas conditions). Accordingly, $R_s/R_0$ is a sensor resistance ratio relatively comparing the resistance value measured by the commercially available semiconductor gas sensor under given gas conditions with the resistance value measured under clean air condition without other gases to be measured except the individual gas to be measured.

For reference, such graph or data showing a change of the sensor resistance ratio depending on gas concentration change is usually provided by the providers or manufacturers of commercially available semiconductor gas sensor for calibration when the commercially available semiconductor gas sensor is purchased. Therefore, in the embodiments, the $R_0$, $k_{ij}$ or $a_{ij}$ values used for calculation in Equation 1 are ready-determined constant values.

If 5 (five) different gases are dissolved in the insulating oil and a total of 5 semiconductor gas sensors are used to measure an individual gas concentration in the gases dissolved in the insulating oil, a logarithm of sensor resistance ratio $(R_s/R_0)_{S1}$ measured for the five gases by one gas sensor S1 among the gas sensors may be expressed as a linear sum of a logarithm of the individual sensor resistance ratio measured for the individual gas at the concentration of the individual gas as shown in the Equation 2.

$$\text{Log}(R_s/R_0)_{s1} = [k_{11} \log(H_2,\text{ppm}) + a_{11}] + [k_{12} \log(CO, \text{ppm}) + a_{12}] + [k_{13} \log(C_2H_2,\text{ppm}) + a_{13}] + [k_{14} \log(C_2H_4,\text{ppm}) + a_{14}] + [k_{15} \log(CH_4,\text{ppm}) + a_{15}] \quad \text{[Equation 2]}$$

In the Equation 2, $k_{11}$ is a change rate of Log (Sensor Resistance Ratio) (i.e., slope of straight line) depending on the change of Log (hydrogen gas concentration) [log($H_2$, ppm)] at the sensor S1.

$a_{11}$ is a Log (Sensor Resistance Ratio) value at which minimum hydrogen gas concentration [($H_2$, ppm)] may be measured by the sensor S1.

$k_{12}$ is a change rate of Log(Sensor Resistance Ratio) (i.e., slope of straight line) depending on the change of Log (carbon monoxide gas concentration) [Log (CO, ppm)] at the sensor S1

$a_{12}$ is a Log (Sensor Resistance Ratio) value at which minimum carbon monoxide gas concentration [(CO, ppm)] may be measured by the sensor S1.

$k_{13}$ is a change rate of Log (Sensor Resistance Ratio) (i.e., slope of straight line) depending on the change of Log (acetylene gas concentration) [Log ($C_2H_2$, ppm)] at the sensor S1.

$a_{13}$ is a Log (Sensor Resistance Ratio) value at which minimum acetylene gas concentration [($C_2H_2$, ppm)] may be measured by the sensor S1.

$k_{14}$ is a change rate of Log (Sensor Resistance Ratio) (i.e., slope of straight line) depending on the change of Log (ethylene gas concentration) [Log ($C_2H_4$, ppm)] at the sensor S1.

$a_{14}$ is a Log (Sensor Resistance Ratio) value at which minimum ethylene gas concentration [($C_2H_4$, ppm)] may be measured by the sensor S1.

$k_{15}$ is a change rate of change of Log (Sensor Resistance Ratio) (i.e., slope of straight line) depending on the change of Log (methane gas concentration) [Log ($CH_4$, ppm)] at the sensor S1.

$a_{15}$ is a Log (Sensor Resistance Ratio) value at which minimum methane gas concentration [($CH_4$, ppm)] may be measured by the sensor S1.

These values may be obtained from the data or he graph as shown in FIG. 5, which is provided by the semiconductor gas sensor manufacturer or providers for calibration. If any gas is not specified in the provided graph for calibration, the k and a values corresponding to such non-specified gas may be set as zero. Although the minimum hydrogen, carbon monoxide, acetylene, ethylene, methane gas concentrations measured by the sensor S1 are exemplified to be the same in FIG. 5, it will be understood by the skilled in the art that the respective minimum gas concentrations may differ.

Similarly to the equation 2, the sensor resistance ratios measured by gas sensors S2, S3, S4, S5 may be expressed as follows.

$$\text{Log}(R_s/R_0)_{s2} = [k_{21} \log(H_2,\text{ppm}) + a_{21}] + [k_{22} \log(CO, \text{ppm}) + a_{22}] + [k_{23} \log(C_2H_2,\text{ppm}) + a_{23}] + [k_{24} \log(C_2H_4,\text{ppm}) + a_{24}] + [k_{25} \log(CH_4,\text{ppm}) + a_{25}] \quad \text{[Equation 3]}$$

$$\text{Log}(R_s/R_0)_{s3} = [k_{31} \log(H_2,\text{ppm}) + a_{31}] + [k_{32} \log(CO, \text{ppm}) + a_{32}] + [k_{33} \log(C_2H_2,\text{ppm}) + a_{33}] + [k_{34} \log(C_2H_4,\text{ppm}) + a_{34}] + [k_{35} \log(CH_4,\text{ppm}) + a_{35}] \quad \text{[Equation 4]}$$

$$\text{Log}(R_s/R_0)_{s4} = [k_{41} \log(H_2,\text{ppm}) + a_{41}] + [k_{42} \log(CO, \text{ppm}) + a_{42}] + [k_{43} \log(C_2H_2,\text{ppm}) + a_{43}] + [k_{44} \log(C_2H_4,\text{ppm}) + a_{44}] + [k_{45} \log(CH_4,\text{ppm}) + a_{45}] \quad \text{[Equation 5]}$$

$$\text{Log}(R_s/R_0)_{s5} = [k_{51} \log(H_2,\text{ppm}) + a_{51}] + [k_{52} \log(CO, \text{ppm}) + a_{52}] + [k_{53} \log(C_2H_2,\text{ppm}) + a_{53}] + [k_{54} \log(C_2H_4,\text{ppm}) + a_{54}] + [k_{55} \log(CH_4,\text{ppm}) + a_{55}] \quad \text{[Equation 6]}$$

The equations 2-6 may be expressed simply by a matrix as in the equation 7.

$$\begin{pmatrix} \log\left(\frac{R_s}{R_0}\right)_{s1} \\ \log\left(\frac{R_s}{R_0}\right)_{s2} \\ \log\left(\frac{R_s}{R_0}\right)_{s3} \\ \log\left(\frac{R_s}{R_0}\right)_{s4} \\ \log\left(\frac{R_s}{R_0}\right)_{s6} \end{pmatrix} = \begin{bmatrix} k_{11} & k_{12} & k_{13} & k_{14} & k_{16} \\ k_{21} & k_{22} & k_{23} & k_{24} & k_{26} \\ k_{31} & k_{32} & k_{33} & k_{34} & k_{36} \\ k_{41} & k_{42} & k_{43} & k_{44} & k_{46} \\ k_{61} & k_{62} & k_{63} & k_{64} & k_{66} \end{bmatrix} \begin{pmatrix} \log(H_2, ppm) \\ \log(CO, ppm) \\ \log(C_2H_2, ppm) \\ \log(C_2H_4, ppm) \\ \log(CH_4, ppm) \end{pmatrix} + \begin{pmatrix} a_{11} + a_{12} + a_{13} + a_{14} + a_{16} \\ a_{21} + a_{22} + a_{23} + a_{24} + a_{26} \\ a_{31} + a_{32} + a_{33} + a_{34} + a_{36} \\ a_{41} + a_{42} + a_{43} + a_{44} + a_{46} \\ a_{61} + a_{62} + a_{63} + a_{64} + a_{66} \end{pmatrix}$$

[Equation 7]

The Equation 7 may be expressed using indices as in the Equation 8.

$$[\text{Log}(R_s/R_0)]_{si} = [k_{ij}][\text{Log } G(\text{ppm})]_i + [\Sigma a_{ij}]_i (i,j=1,\ldots 5) \quad \text{[Equation 8]}$$

Accordingly, the logarithm of concentration of the individual gases ([Log G (ppm)]$_i$ (i=1, . . . , 5) dissolved in the insulating oil may be calculated by the equation 9.

$$[\text{Log } G(\text{ppm})]_i = [k_{ij}]^{-1}[[\text{Log}(R_s/R_0)]_i - [\Sigma a_{ij}]_i] \quad (i,j=1,\ldots,5) \quad \text{[Equation 9]}$$

In the equations 8 and 9, as described above, $R_0$ is a constant sensor resistance value measured when a concentrations of an individual gas is fixed, for example, at 1000 ppm under clean air condition without other gases to be measured except the individual gas, $R_s/R_0$ is a sensor resistance ratio, i is a number assigned to the individual semiconductor gas sensors used for the measurement of gas concentration, and j is a number assigned to the individual gases subjected to the gas concentration measurement. In this example, i and j are from 1 to 5. G is a concentration (ppm) of the individual gases, $[\text{Log } G]_i$ is a matrix of the logarithm of concentration of the individual gas to be measured, $k_{ij}$ is a change rate of the logarithm of sensor resistance ratio in response to the change of the logarithm of concentration of the j-th gas at the i-th semiconductor gas sensor, which is a constant determined at the i-th semiconductor gas sensor depending on the j-th gas or a value calibrated from the constant.

$[k_{ij}]$ and $[k_{ij}]^{-1}$ are respectively a matrix of $k_{ij}$ and an inverse matrix thereof with i and j varying from 1 to 5 respectively, $[\text{Log}(R_s/R_0)]_i$ is a matrix of the logarithm of the sensor resistance ratio with i varying from 1 to 5, $a_{ij}$ is a logarithm of sensor resistance ratio at which minimum concentration of the j-th gas may be measured at the i-th semiconductor gas sensor, which is a constant determined at the i-th semiconductor gas sensor depending on the j-th gas or a value calibrated from the constant. $\Sigma a_{ij}$ is a sum of $a_{ij}$ with i being fixed and j varying from 1 to 5, and $[\Sigma a_{ij}]_i$ is a matrix of with i varying from 1 to 5.

As such, the concentration of the individual gases dissolved in the insulating oil may be obtained through the calculation as described above.

The inverse matrix may be obtained using a mathematical algorithm such as Gauss-Jordan elimination or may be calculated easily using a commercially available software (e.g. MATLAB). This calculation method or software is well known in the art. A calculation device according to exemplary embodiments may comprise a processor or a computer using the software.

If the graph for calibration provided by the semiconductor gas sensor provider or manufacturer includes other gases in addition to those described above (i.e., i=j>5), i and j in the Equation 9 may be increased.

When i and j are extended to vary from 1 to n, the Equation 1 described above is obtained.

With the method and apparatus for measuring gas concentration, the concentration of the individual gases dissolved in the insulating oil may be measured easily and quantitatively with high reliability using a commercially available, i.e., generally-used semiconductor gas sensor without being subject to the difficulties of having to use or choose specific semiconductor gas sensors reacting with specific gases.

Hereinafter, the embodiments will be further explained by examples and experiments. The following examples and experiments are for illustrative purposes only and not intended to limit the scope of this disclosure.

Preparation of Composite Separation Membrane Structure

In the example, a composite separation membrane structure as shown in FIG. 1 is prepared.

A metal mesh is used as the support having a mesh structure 5a, where the metal mesh is made of stainless-steel and has a dense lattice-type mesh with a thickness of 0.1 mm and a mesh size of 4 μm×4 μm (length and breadth).

When a self-assembled monolayer 5c, which serves as a separation membrane for oil/gas separation, is coated directly on the metal mesh 5a, it may be impossible to obtain a membrane having very fine and dense pores. Thus, a coating layer 5b of a porous sol-gel material which has pores of comparatively less fine and dense than the those of the self-assembled monolayer is formed first on the metal mesh 5a.

A process of forming the coating layer 5b of the porous sol-gel material is, for example, as follows.

As spherical silicon alkoxide is hydrolyzed to form silicon hydroxide, the hydroxyl groups (—OH) in the produced molecules react with each other to form a polymer in sol state. The hydrolysis proceeds as follows.

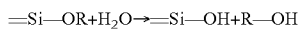
[Scheme 1]

During condensation polymerization, gelation occurs as silicon oxides are interconnected to form a 3-dimensional structure depending on reaction atmospheres. The condensation polymerization proceeds as follows.

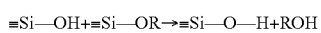
[Scheme 2]

Complete gelation is achieved through heat treatment after the organically modified hybrid sol-gel material is coated on the support having a mesh structure. During the gelation, fine pores are formed as a 3-dimensional structure of molecules are formed.

As a specific example, the organically modified hybrid sol-gel material is synthesized as follows.

Methyltrimethoxysilane (MTMOS) and tetramethoxysilane (TEOS) as silicon alkoxide precursor and 3-methacryloxypropyltrimethoxysilane (MEMOS) as organically modified silane precursor are mixed at a molar ratio of 5:4:1, and are put in a 3-necked round-bottom flask equipped with a condenser and a thermometer together with a mixture of methanol and isopropyl alcohol (IPA) (1:1, based on weight), and then are stirred continuously for 30 minutes using a magnetic stirrer after adjusting temperature to 30° C.

Figure 6:
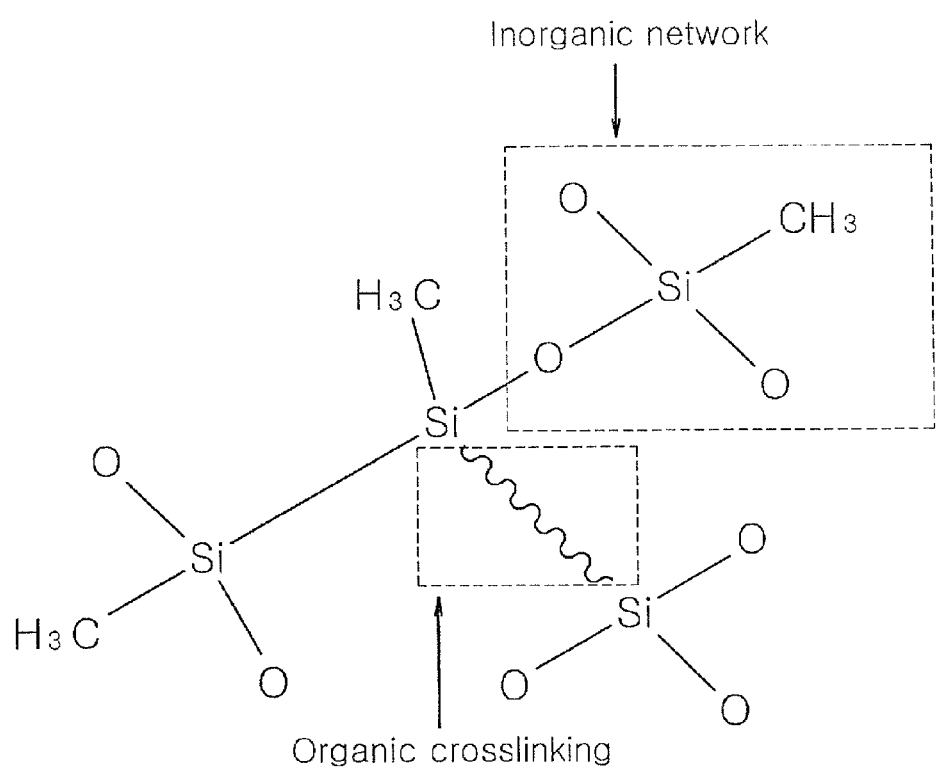
FIG. 6 illustrates a molecular structure of a porous material layer used in an example.

Then, after slowly adding dropwise a catalyst solution using a dropping funnel, the catalyst being prepared by mixing 20 g of a 1:1 (based on weight) mixture solution of methanol and isopropyl alcohol with deionized water whose pH is adjusted to about 3-4 with strong phosphoric acid of 98% or stronger in a manner that a molar ratio of the catalyst solution to the silane precursor is 2:1 ($H_2O$:alkoxide), the mixture is stirred continuously to go through a reaction for about 2 hours at a maintained temperature of 30° C. The unit molecular structure of the resultant organically modified hybrid separation membrane is shown in FIG. 6.

On a surface of the prepared porous sol-gel material coating layer 5b, a self-assembled monolayer of a fluorohydrocarbon-based silane (EGC-1720, 3M) which is both oleophobic and hydrophobic is coated to prepare a composite separation membrane structure so as to prevent contamination by and penetration of impurities such as oil, water, dust, etc. and to enhance the separation efficiency of the gases dissolved in the insulating oil.

Test of Composite Separation Membrane Structure

The following test is performed to verify the effect of the composite separation membrane structure according to the example.

Figure 7:
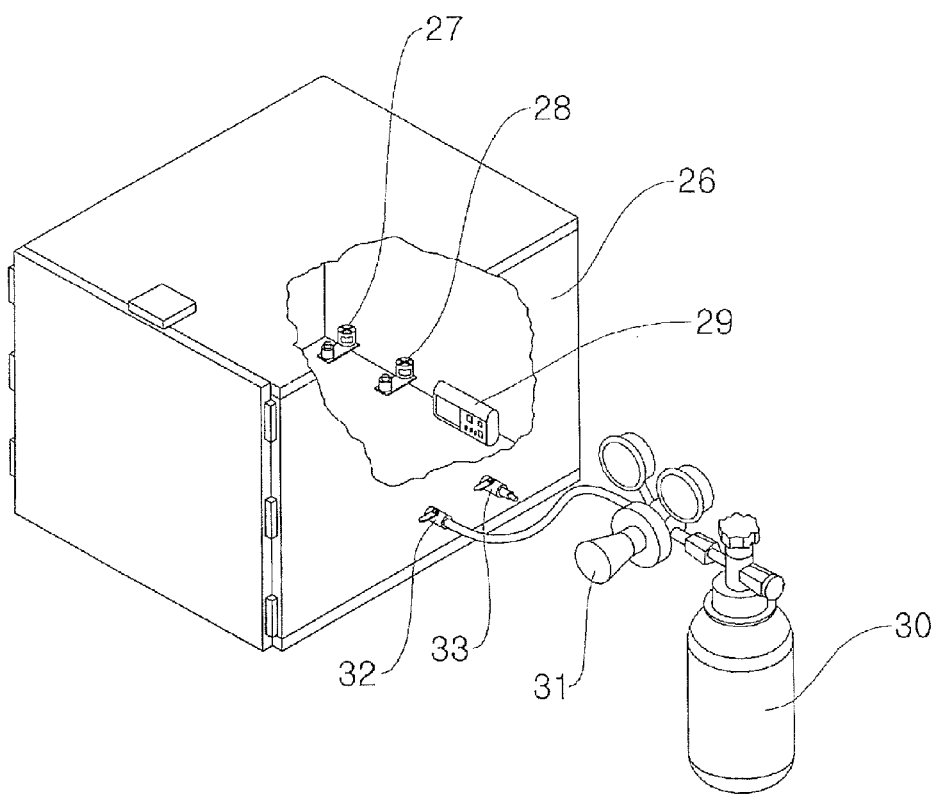
FIG. 7 schematically shows an apparatus constructed to evaluate the effect of the composite separation membrane structure according to an example.

FIG. 7 schematically shows an apparatus constructed to evaluate the effect of the composite separation membrane structure according to an example.

As shown in FIG. 7, a pressure vessel 30 containing carbon dioxide gas is connected to a transparent and sealed acryl box 26 having a volume. After injecting carbon dioxide into the box 26 to an adequate concentration using a pressure controller 31 and opening an on/off valve 32, the valve 32 is closed.

Inside the box 26, a gas sensor apparatus constructed by assembling the composite separation membrane structure prepared above with a semiconductor carbon dioxide gas sensor (MG811, Hanwei Electronics Co., Ltd.) as shown in FIGS. 2a-2c (Example) and the same gas sensor apparatus without the composite separation membrane structure (Comparative Example) are disposed at the locations 27 and 28, respectively.

Then, another on/off valve 33 for gas discharge equipped at the box is slightly opened so that the concentration of carbon dioxide in the sealed box decreased gradually. Under this situation, the results from the two gas sensor apparatuses 27, 28 are tested and compared.

Also, for quantitative comparison of carbon dioxide concentration under this test condition, a commercially available electrochemical carbon dioxide gas sensor 29 is disposed inside the box 26 and the amount of carbon dioxide which is decreasing depending on the change of time is measured.

Figure 8:
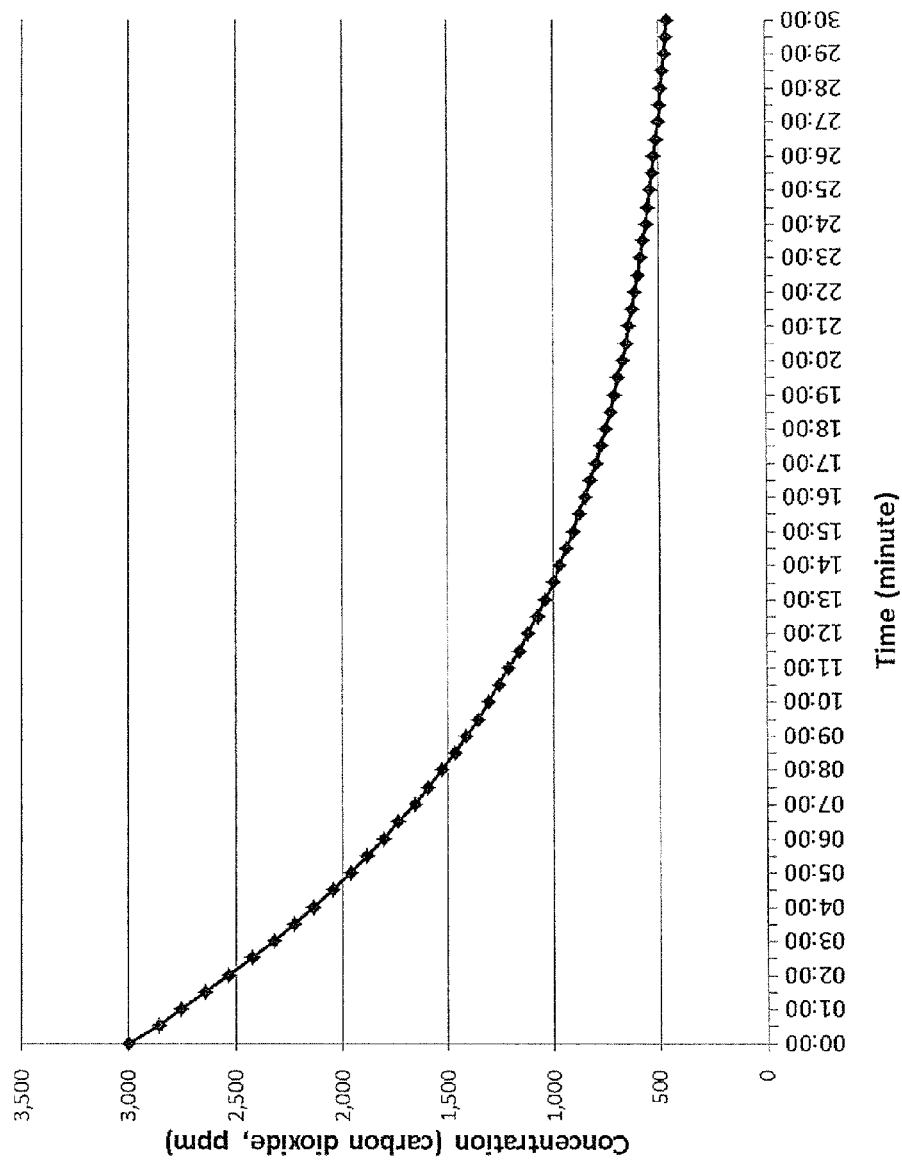
FIG. 8 shows a result of measuring a change of carbon dioxide concentration with time change using an electrochemical gas sensor in an example.

FIG. 8 shows a result of measuring a change of carbon dioxide concentration with time change using an electrochemical gas sensor in an example. In FIG. 8, the x-axis is time (min) and the y-axis is carbon dioxide concentration (ppm).

As seen in FIG. 8, the concentration of the carbon dioxide gas injected into the box 26 decreases gradually as time goes as the valve 33 is opened.

Figure 9:
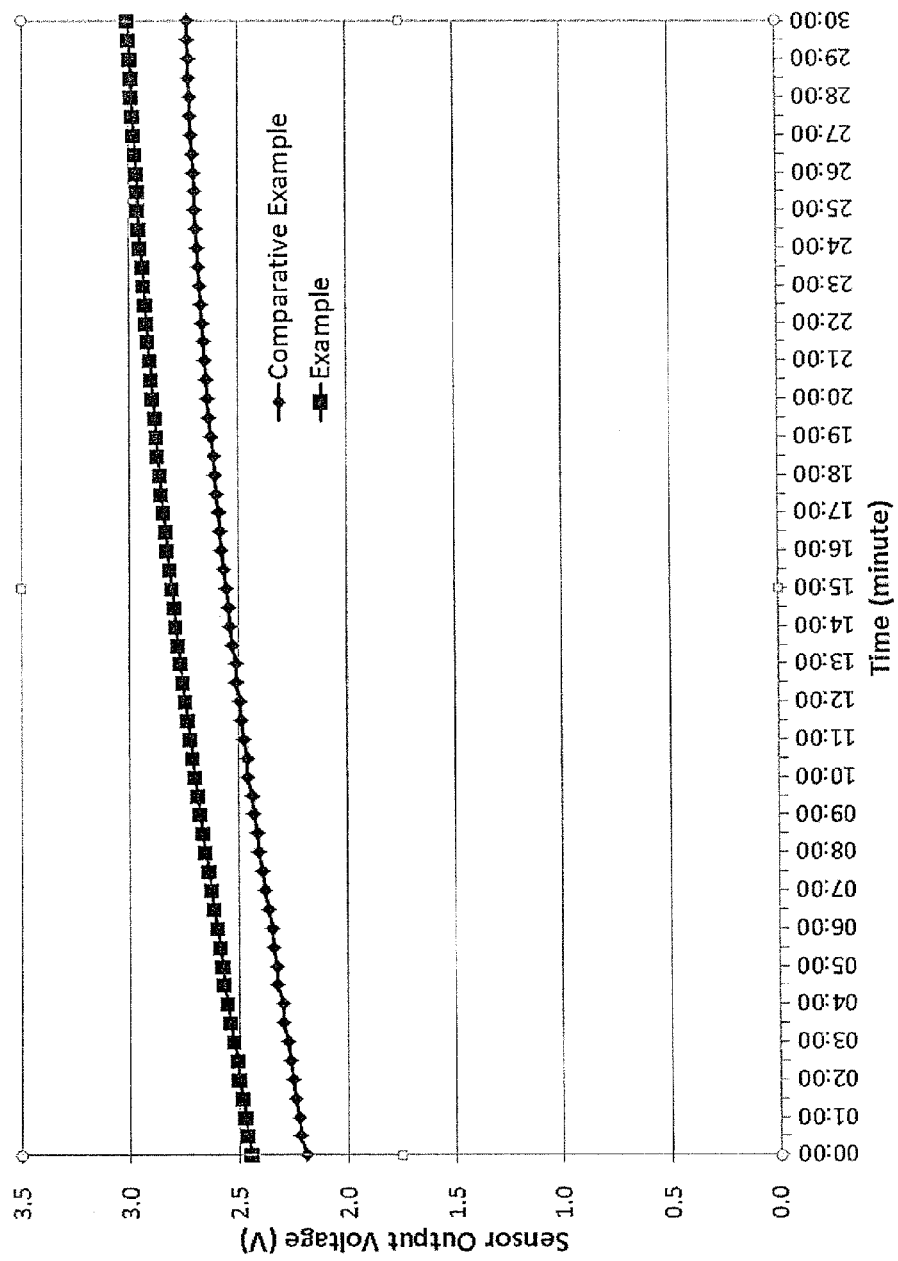
FIG. 9 shows a result of voltages of a gas sensor measured under the same experiment condition as in FIG. 8, comparing cases of use or no use of a composite separation membrane structure.

FIG. 9 shows a result of voltages of a gas sensor measured under the same experiment condition as in FIG. 8, comparing cases of use or no use of a composite separation membrane structure. In FIG. 9, the x-axis is time (min) and the y-axis is sensor output voltage (V).

It can be seen that the gas sensor apparatus of Example gives a relatively higher output value than the gas sensor apparatus of Comparative Example. This means that the carbon dioxide concentration measured by the gas sensor apparatus with the composite separation membrane structure is slightly lower than the concentration of carbon dioxide actually present in the box.

This suggests that the separation membrane functions as a kind of resistance factor, although insignificant, in the gas measurement. Since the resistance effect is uniform over the whole carbon dioxide concentration range tested and is not significant, the resistance effect may be removed in a manner that $k_{ij}$ and $a_{ij}$ are calibrated from its original value (where the gas sensor is used without the separation membrane) through a calibration experiment (where the gas sensor is uses together with the separation membrane) by the user secondarily.

The composite separation membrane structure according to the embodiments of the present invention, through which the insulating oil may not pass but the gases dissolved therein may pass, has very small pressure difference across the membrane and experiences no degradation of mechanical strength. Further, contamination by the insulating oil or water included in the insulating oil may be prevented.

Since a gas sensor apparatus comprising the composite separation membrane structure and a commercially available semiconductor gas sensor may be directly attached to the upper or lower portion of a power transformer, installation and filed application of the sensor are simple, convenient and economical. Accordingly, when the gas sensor apparatus is used, it is not necessary to use an additional mechanical apparatus such as a vacuum pump for extracting the gases dissolved in the insulating oil of the power transformer.

In addition, the method and the apparatus for measuring gas concentration according to the embodiments allow for easy measurement of the concentration of individual gases dissolved in the insulating oil with high reliability using a generally-used semiconductor gas sensor, without being subject to difficulties of using or choosing specific semiconductor gas sensors reacting with specific gases.

Accordingly, it is possible to monitor whether and where faults occurred in an operating power transformer in real time at the field. Further, the service life of the insulating oil in the power transformer may be predicted. As a result, breakdown of the power transformer may be prevented and maintenance of the power transformer may be achieved economically with high reliability.

While the present invention has been described with respect to the specific embodiments, it will be apparent to those skilled in the art that various changes and modifications may be made without departing from the spirit and scope of the disclosure as defined in the following claims.

What is claimed is:

1. A composite separation membrane structure for a gas sensor comprising:
   a support having a mesh structure that has a thickness of about 0.05-1 mm;
   a coating layer of a porous sol-gel material disposed on an outer surface of the support, wherein the coating layer that has a thickness of about 10 to 1,000 nm;
   a self-assembled monolayer disposed on the coating layer of the porous sol-gel material, wherein the self-assembled monolayer that has a thickness of about 1 to 10 μm;
   wherein the coating layer has pores that are larger than pores of the self-assembled monolayer.

2. The composite separation membrane structure for a gas sensor according to claim 1, wherein the self-assembled monolayer is both oleophobic and hydrophobic.

3. The composite separation membrane structure for a gas sensor according to claim 2, wherein the self-assembled monolayer comprises a fluorohydrocarbon-based silane.

4. The composite separation membrane structure for a gas sensor according to claim 3, wherein the support having the mesh structure is a metal or ceramic support.

5. The composite separation membrane structure for a gas sensor according to claim 4, wherein the porous sol-gel material comprises a polymer material obtained by the sol-gel method from a precursor of at least one alkoxysilane selected from a group consisting of methyltrimethoxysilane, tetramethoxysilane, dimethyldimethoxysilane, tetraethoxysilane, methyltriethoxysilane, dimethyldiethoxysilane, phenyltrimethoxysilane, diphenyldimethoxysilane, phenyltriethoxysilane, diphenyldiethoxysilane, decyltrimethoxysilane and isobutyltrimethoxysilane.

6. A composite separation membrane structure for a gas sensor comprising:
   a support having a mesh structure;
   a coating layer of a porous sol-gel material disposed on an outer surface of the support;
   a self-assembled monolayer disposed on the coating layer of the porous sol-gel material,
   wherein the self-assembled monolayer is both oleophobic and hydrophobic,
   wherein the self-assembled monolayer comprises a fluorohydrocarbon-based silane,
   wherein the support having the mesh structure is a metal or ceramic support,
   wherein the porous sol-gel material is a polymer material obtained by the sol-gel method from a precursor of at least one alkoxysilane selected from a group consisting of methyltrimethoxysilane, tetramethoxysilane, dimethyldimethoxysilane, tetraethoxysilane, methyltriethoxysilane, dimethyldiethoxysilane, phenyltrimethoxysilane, diphenyldimethoxysilane, phenyltriethoxysilane, diphenyldiethoxysilane, decyltrimethoxysilane and isobutyltrimethoxysilane, wherein the composite separation membrane structure comprising three (3) layers:
(a) a first layer consisting of the support, said first layer having a thickness of about 0.05 to 1 mm;
(b) a second layer consisting of the coating layer, said second layer being coated on the first layer and having a thickness of about 10 to 1,000 nm; and
(c) a third layer consisting of the self-assembled monolayer, said third layer being coated on the second layer and having a thickness of about 0.05 to 1 mm;
wherein the coating layer has pores that are larger than pores of the self-assembled monolayer.

7. A gas sensor apparatus comprising:
a semiconductor gas sensor; and
the composite separation membrane structure according to claim 6 disposed apart from the semiconductor gas sensor.

8. The gas sensor apparatus according to claim 7, wherein the gas sensor apparatus comprises:
a housing wherein the semiconductor gas sensor and the composite separation membrane structure are accommodated or mounted;
a lower plate supporting the semiconductor gas sensor; and
an upper plate covering the composite separation membrane structure; and
the lower plate and the upper plate are respectively engaged with the housing.

9. The gas sensor apparatus according to claim 8, wherein the gas sensor apparatus further comprises a gas seal pad disposed on one or both sides of the composite separation membrane structure.

10. The gas sensor apparatus according to claim 8, wherein the gas sensor apparatus further comprises a seal member in the housing.

11. The gas sensor apparatus according to claim 7, wherein the gas sensor apparatus comprises:
one said composite separation membrane structure; and
a semiconductor gas sensor array wherein two or more of the semiconductor gas sensors are arranged.

12. The gas sensor apparatus according to claim 11, wherein the gas sensor apparatus comprises:
a first housing wherein the semiconductor gas sensor array is accommodated or mounted;
a second housing wherein the composite separation membrane structure is accommodated or mounted;
an end cap engaged with a lower portion of the first housing; and
an adapter engaged with an upper portion of the second housing; and
the first housing and the second housing are engaged with each other.

13. The gas sensor apparatus according to claim 12, wherein the gas sensor apparatus further comprises a gas seal pad disposed on one or both sides of the composite separation membrane structure.

14. The gas sensor apparatus according to claim 12, wherein the gas sensor apparatus further comprises a seal member in at least one of the first housing and the second housing.

15. The gas sensor apparatus according to claim 12, wherein the gas sensor apparatus further comprises a connecting member connecting the first housing with the end cap.

16. The gas sensor apparatus according to claim 7, wherein the gas sensor apparatus performs sensing in contact with an insulating oil of a power transformer or a fume of the insulating oil.

17. A method for measuring gas concentration, comprising:
obtaining a sensor resistance value $R_s$ by sensing gases dissolved in an insulating oil using a gas sensor apparatus with at least one semiconductor gas sensor and the composite separation membrane structure according to claim 6; and
obtaining a concentration of an individual gas dissolved in the insulating oil from the sensor resistance value $R_s$ using Equation 1:

$$[\text{Log } G]_i = [k_{ij}]^{-1}[[\text{Log}(R_s/R_0)]_i - [\Sigma a_{ij}]_i](i,j=1,\ldots,n) \quad \text{[Equation 1]}$$

wherein $R_0$ is a sensor resistance value measured when a concentration of an individual gas is fixed under air condition without other gases to be measured except the individual gas, which is a constant;
$R_s/R_0$ is a sensor resistance ratio,
i is a number assigned to the individual semiconductor gas sensors used for the measurement of gas concentration,
j is a number assigned to the individual gases subjected to the gas concentration measurement,
n is a total number of gases measured,
G is a concentration of an individual gas to be measured,
$[\text{Log } G]_i$ is a matrix of a logarithm of concentrations of individual gases to be measured,
$k_{ij}$ is a change rate of a logarithm of the sensor resistance ratio depending on the change of a logarithm of concentration of the j-th gas at the i-th semiconductor gas sensor, which is a constant determined by the i-th semiconductor gas sensor depending on the j-th gas or a value calibrated from the constant,
$[k_{ij}]^{-1}$ is an inverse matrix of a matrix of $k_{ij}$, with i and j varying from 1 to n respectively,
$[\text{Log}(R_s/R_0)]_i$ is a matrix of the logarithm of the sensor resistance ratio with i varying from 1 to n,
$a_{ij}$ is a logarithm of sensor resistance ratio at which minimum concentration of the j-th gas may be measured by the i-th semiconductor gas sensor, which is a constant determined by the i-th semiconductor gas sensor depending on the j-th gas or a value calibrated from the constant,
$\Sigma a_{ij}$ is a sum of $a_{ij}$ with i being fixed and j varying from 1 to n, and $[\Sigma a_{ij}]_i$ is a matrix of $\Sigma a_{ij}$ with i varying from 1 to n.

18. The method for measuring gas concentration according to claim 17, wherein a gas sensor apparatus is used, the gas sensor apparatus comprising:
the semiconductor gas sensor; and
a composite separation membrane structure, which comprises: a support having a mesh structure; a coating layer of a porous sol-gel material disposed on the support; and a self-assembled monolayer disposed on the coating layer of the porous sol-gel material, the composite separation membrane structure being disposed apart from the semiconductor gas sensor.

19. An apparatus for measuring gas concentration comprising:
a gas sensor apparatus with at least one semiconductor gas sensor and the composite separation membrane structure according to claim 6; and
a calculation device obtaining a concentration of an individual gas dissolved in insulating oil using Equation 1 from a resistance value $R_s$, which is obtained by sensing the gases dissolved in the insulating oil using the semiconductor gas sensor, $$[\text{Log } G]_i = [k_{ij}]^{-1}[[\text{Log}(R_s/R_0)]_i - [\Sigma a_{ij}k]_i](i,j=1,\ldots,n) \quad \text{[Equation 1]}$$

wherein $R_0$ is a sensor resistance value measured when a concentration of an individual gas is fixed under air condition without other gases to be measured except the individual gas, which is a constant;

$R_s/R_0$ is a sensor resistance ratio, i is a number assigned to the individual semiconductor gas sensors used for the measurement of gas concentration, j is a number assigned to the individual gases subjected to the gas concentration measurement, n is a total number of gases measured, G is a concentration of an individual gas to be measured, $[\text{Log } G]_i$ is a matrix of a logarithm of concentrations of individual gases to be measured, $k_{ij}$ is a change rate of a logarithm of the sensor resistance ratio depending on the change of a logarithm of concentration of the j-th gas at the i-th semiconductor gas sensor, which is a constant determined by the i-th semiconductor gas sensor depending on the j-th gas or a value calibrated from the constant, $[k_{ij}]^{-1}$ is an inverse matrix of a matrix of $k_{ij}$, with i and j varying from 1 to n respectively, $[\text{Log}(R_s/R_0)]_i$ is a matrix of the logarithm of the sensor resistance ratio with i varying from 1 to n, $a_{ij}$ is a logarithm of sensor resistance ratio at which minimum concentration of the j-th gas may be measured by the i-th semiconductor gas sensor, which is a constant determined by the i-th semiconductor gas sensor depending on the j-th gas or a value calibrated from the constant, $\Sigma a_{ij}$ is a sum of $a_{ij}$ with i being fixed and j varying from 1 to n, and $[\Sigma a_{ij}]_i$ is a matrix of $\Sigma a_{ij}$ with i varying from 1 to n.

20. The apparatus for measuring gas concentration according to claim 19, wherein the sensor resistance value $R_s$ is obtained using the semiconductor gas sensor.

* * * * *